(12) United States Patent
Gellman et al.

(10) Patent No.: US 12,357,228 B2
(45) Date of Patent: Jul. 15, 2025

(54) VACUUM DRESSING WITH ATMOSPHERIC CONTROL FEEDBACK

(71) Applicant: Cardiac Assist Holdings, LLC, Ann Arbor, MI (US)

(72) Inventors: Barry N. Gellman, Ann Arbor, MI (US); Allen B. Kantrowitz, Ann Arbor, MI (US); Kurt A. Dasse, Ann Arbor, MI (US)

(73) Assignee: Cardiac Assist Holdings, LLC, Ann Arbor, MI (US)

( * ) Notice: Subject to any disclaimer, the term of this patent is extended or adjusted under 35 U.S.C. 154(b) by 582 days.

(21) Appl. No.: 17/744,815

(22) Filed: May 16, 2022

(65) Prior Publication Data

US 2022/0273230 A1    Sep. 1, 2022

Related U.S. Application Data

(63) Continuation-in-part of application No. PCT/US2020/060673, filed on Nov. 16, 2020.
(Continued)

(51) Int. Cl.
*A61B 5/00* (2006.01)
*A61B 5/0531* (2021.01)
(Continued)

(52) U.S. Cl.
CPC ............ *A61B 5/445* (2013.01); *A61B 5/0531* (2013.01); *A61B 5/4836* (2013.01);
(Continued)

(58) Field of Classification Search
CPC . A61M 1/95; A61M 2205/3553; A61B 5/445; A61B 5/053; A61B 5/0531; A61B 5/4836; A61B 5/6834
See application file for complete search history.

(56) References Cited

U.S. PATENT DOCUMENTS

2013/0165821 A1* 6/2013 Freedman ........... A61M 3/0279
                                                                 604/20
2013/0261534 A1   10/2013 Niezgoda et al.
(Continued)

FOREIGN PATENT DOCUMENTS

| WO | 2018210693 A1 | 11/2018 |
| WO | 2019096828 A1 | 5/2019 |
| WO | 2019194883 A1 | 10/2019 |

OTHER PUBLICATIONS

Int'l Search Report for PCT/US2020/060673, dated Mar. 9, 2021.
Supplementary Search Report issued in corresponding European Patent Appln. No. 20886613.7, dated Oct. 31, 2023.

*Primary Examiner* — Gerald Johnson
(74) *Attorney, Agent, or Firm* — MaxGoLaw PLLC

(57) ABSTRACT

Percutaneous access devices (PAD), bandages, or other implantable medical devices are provided that are equipped with filters, environmental controls, and sensors that promote the formation of a natural biologic seal between the skin and the device to form a barrier to microbial invasion into the body. Levels of humidity and pressure are monitored and dynamically controlled to optimize wound closure about an implanted device or when a PAD is not present a wound itself. Methods and systems for actively assessing wound closure are incorporated into the design of percutaneous skin access devices (PAD), bone anchors, or a wound dressing or bandage alone without at PAD. Pressure and humidity sensors provide active feedback for making changes to the ecology of the wound site or PAD insertion site. A filter is used to aerate the wound while also preventing pathogens in the ambient air from reaching the wound.

19 Claims, 8 Drawing Sheets

Related U.S. Application Data

(60) Provisional application No. 62/935,680, filed on Nov. 15, 2019.

(51) Int. Cl.
*A61F 13/05* (2024.01)
*A61M 1/00* (2006.01)
*A61B 5/01* (2006.01)

(52) U.S. Cl.
CPC ............ *A61B 5/6834* (2013.01); *A61F 13/05* (2024.01); *A61M 1/95* (2021.05); *A61B 5/015* (2013.01); *A61B 2562/029* (2013.01); *A61M 2205/3553* (2013.01); *A61M 2205/50* (2013.01); *A61M 2205/8206* (2013.01)

(56) References Cited

U.S. PATENT DOCUMENTS

2016/0030722 A1    2/2016  Anderson et al.
2016/0321804 A1*  11/2016  Shupp .................. A61B 5/0077
2017/0172488 A1    6/2017  Kantrowitz et al.
2017/0231823 A1    8/2017  Zawoy et al.
2019/0290496 A1    9/2019  Brownhill et al.
2021/0023281 A1*   1/2021  Locke .................... A61M 1/73

* cited by examiner

VACUUM DRESSING WITH ATMOSPHERIC CONTROL FEEDBACK

CROSS REFERENCE TO RELATED APPLICATIONS

This application is a continuation in part of PCT Application Serial Number PCT/US2020/060673, filed Nov. 16, 2020; that in turn claims priority of U.S. Provisional Application Ser. No. 62/935,680, filed Nov. 15, 2019, the contents of which are hereby incorporated by reference.

FIELD OF THE INVENTION

The present invention in general relates to medical devices and systems, and in particular to percutaneous access devices (PAD), vacuum dressings, or other implantable medical devices having atmospheric control feedback to encourage and maximize the rate of healing and skin formation in an entry or wound area.

BACKGROUND OF THE INVENTION

Intravenous catheters act as an attachment point for microorganisms, leading to biofilm formation and infection at the site of insertion or along the surface of the device. Infection of the catheter hub and catheter-related bloodstream infections are major complications for patients with indwelling catheters (e.g., Safdar and Maki, *Intensive Care Med.* 2004 January; 30(1):62-7; Saint et al., Infect Control Hosp Epidemiol. 2000 June; 21(6):375-80).

Prior attempts at controlling catheter-related infection are directed to sterilization techniques such as by topical or fluidic antibacterials applied to the insertion site or integrated into the catheter itself. The antimicrobial activity of ethyl alcohol (ethanol) as well as other alcohols is well known. Isopropyl alcohol at a concentration of 60-70% is widely used as an antimicrobial agent for sanitization of surfaces and skin. A concentration of 10% ethyl alcohol inhibits the growth of most microorganisms, while concentrations of 40% and higher are generally considered bactericidal (Sissons et al., *Archives of Oral Biology*, Vol. 41, 1, JN 1996; 27-34).

Catheterization can be kept in place for as little as a few seconds for drainage or delivery. It is increasingly common, however, for percutaneous access such as peripherally inserted central catheters (PICC), skeletal guide wires, cardiac assist device lines, or other instruments to be kept in place for weeks or months. The increased time in which such devices are maintained across the skin increases the likelihood of instrument related infection.

Another common implantable device that breaks the skin and may be a source of infection are blood pumps that may be surgically implanted in, or adjacent to the cardiovascular system to augment the pumping action of the heart. The blood pump is sometimes referred to as a mechanical auxiliary ventricle assist device, dynamic aortic patch, balloon pump, mechanical circulatory assist device, or a total mechanical heart. Alternatively, the blood pump can be inserted endovascularly. Typically, the blood pump systems include a driveline that serves as a power and/or signal conduit between the blood pump internal to the patient and a controller/console external to the patient. Additional external medical devices may illustratively include implantable pumps such as insulin pumps and colostomy bags.

Percutaneous access devices (PAD) have been introduced that serve as semi-permanent or extended entry points for the aforementioned catheters and implantable and externally worn medical devices. For example, a percutaneous access device (PAD) may be surgically implanted in the body at the location in the skin where the driveline penetrates the skin to provide a through-the-skin coupling for connecting the supply tube to an extra-corporeal fluid pressure source. In a further example, electrical leads from electrodes implanted in the myocardium are likewise brought out through the skin by means of the PAD. Percutaneous access devices may also illustratively be used for other devices including peritoneal dialysis catheters, Steinman pin, Kirschner wires, and chronic indwelling venous access catheters that require skin penetration. More generally, medical appliances which are implanted so as to cross the skin surface and therefore violate the "barrier function" of the skin, may also illustratively be used for other medical purposes including peritoneal dialysis catheters and, chronic indwelling venous access catheters, neurologic prostheses, osseointegrated prostheses, drug pumps, and other treatments that require skin penetration.

The use of percutaneous access devices decreases or prevents penetration or complications due to the presence of an agent in a subject. As used herein an "agent" is illustratively: an infectious agent such as bacteria, virus, fungus, other organism; or foreign material. Illustrative examples of foreign material include bandage; soil; water, saliva, urine, or other fluid; feces; chemicals; or other matter known in the art. Illustrative examples of infectious agents that are prevented from penetrating or produce complications include *P. aeruginosa, E. cloacae; E. faecalis; C. albicans; K. pneumonia; E. coli; S. aureus*; or other infectious agents. As used herein, the term "subject" refers to a human or non-human animal, optionally a mammal including a human, non-primate such as cows, pigs, horses, goats, sheep, cats, dogs, avian species and rodents; and a non-human primate such as monkeys, chimpanzees, and apes; and a human, also denoted specifically as a "human subject".

A force is typically applied to a PAD to counteract fluid collection or flow along a percutaneous instrument tissue interface. It is common for fluid to develop in the space surrounding a percutaneous instrument often beginning immediately after insertion. The presence of this fluid allows migration, flow, or other penetration of agents normally excluded by the intact skin to areas below the skin. The penetration by these agents may lead to development of infectious disease, inflammation at the site of insertion, or other unwanted complications. A force that is applied is illustratively a vacuum. A vacuum illustratively prevents fluid from moving along an interface between tissue and the embedded catheter or other instrument. The negative pressure of the vacuum allows the natural pressures of biological material or other atmospheric pressure to move unwanted material away from the areas at or below the site of insertion.

The surface of the driveline, or of the PAD used in cardiac assist systems may have characteristics which promote the formation of a natural biologic seal between the skin and the device to form a barrier to microbial invasion into the body at the skin penetration site. However, a common problem associated with implantation of a percutaneous access device (PAD) is skin regeneration about the periphery of the device to form an immunoprotective seal against infection. New cell growth and maintenance is typically frustrated by the considerable mechanical forces exerted on the interfacial layer of cells. In order to facilitate skin regeneration about the exterior of a PAD, subject cells are often harvested and grown in culture onto PAD surfaces for several days prior to implantation in order to allow an interfacial cell layer to colonize PAD surfaces in advance of implantation. Unfortunately, cell culturing has met with limited acceptance owing to the need for a cell harvesting surgical procedure preceding the implantation procedure. Additionally, maintaining tissue culture integrity is also a complex and time-consuming task.

As an alternative to cell culturing on a percutaneous access device, vacuum assisted wound treatment about a percutaneous access device has been attempted. While DACRON® based random felt meshes have been used to promote cell regrowth in the vicinity of a wound, such felts have uncontrolled pore sizes that harbor bacterial growth pockets.

U.S. Pat. No. 7,704,225 to Kantrowitz solves many of these aforementioned problems by providing cell channeling contours, porous biodegradable polymers and the application of vacuum to promote cellular growth towards the surface the neck of a PAD. The facilitating of rapid cellular colonization of a PAD neck allows the subject to act as their own cell culture facility, and as such affords more rapid stabilization of the PAD, and lower incidence of separation and infection.

The aforementioned PAD are constructed with one or more sleeves. A sleeve is optionally an inner sleeve or an outer sleeve. As used herein, the terms "inner" and "outer" are relative terms in terms of encompassing relative dimensions and should not be construed contextually as to positioning relative to the epidermis. An inner sleeve is optionally made of a porous material or scaffold that is optionally penetrated by fluids or gasses. A scaffold is optionally a tissue scaffold that allows or promotes attachment of cells, illustratively, fibroblasts to the surface of an inner sleeve. An inner sleeve is optionally treated. An inner sleeve treatment illustratively includes compounds or surface textures that promote attachment of fibroblasts or other cellular material. Optionally, the inner sleeve is made of a woven material. A woven material is optionally penetratable by cells, fluids, gas, or other materials.

It is appreciated that an inner sleeve is optionally the only sleeve present in a PAD. An inner sleeve is optionally a porous scaffold that is suitable for moving fluid or gas through the sleeve away from the surrounding environment. Materials operable for use as an inner sleeve illustratively include collagen, PEBAX, nylons, polypropylenes, polyurethanes, polyethylenes (HDPE, UHWPE, LDPE, or any blend of the aforementioned polyethylenes), PET, NiTi, MYLAR, Nickel Titanium Alloy, other polymers such as other thermoplastic polymers, fabrics, silicones such as silicone rubber, latex, glass, or other materials known in the art. It is appreciated that polymeric materials with a gradient of cross-linking density through the material afford certain advantages with respect to promoting vacuum or hydrodynamic draw and fibroblast infiltration. By way of example, a polymer having a greater rigidity proximal to the central axis of the device relative to the distal surface inhibits pressure differential induced collapse. In some embodiments, an inner sleeve is made from chemically inert material. In some embodiments, the porous scaffold is in direct contact with the skin of the subject or traverses the skin of the subject. In some embodiments an inner sleeve is textured or woven in such a way so as to provide attachment sites for fibroblasts. A texture is optionally a nanotexture. Illustrative nanotextures have pore sizes that are uniformly less than 500 nanometers to provide an anchor point for a fibroblast pseudopod extension, while having dimensions that disfavor bacterial colonization. A nanotextured surface as used herein has features indentations of from 50 to 500 nanometer median dimension. In some embodiments, the indentations have a median dimension of between 100 and 300 nanometers.

In some embodiments of PAD, a texture is in the form of a scaffold. A scaffold is illustratively formed of gold. A gold scaffold is optionally formed by making a sleeve from a gold/silver alloy that is dipped in an acid such as a mineral acid which selectively dissolves the silver leaving a gold structure with appropriate porosity. Alternatively, a scaffold is formed from an acid etchable, biocompatible nanocrystal such as silver or silica is dispersed in a polymer melt such as polycarbonate and a neck either formed directly therefrom, or the nanocrystal-doped polymer is coated onto a neck substrate. Through subjecting the nanocrystal-doped polymer to an acid or base solution, depending on the solubility of the nanocrystal, voids are formed in the polymer reflective of the original nanocrystal dopant. For instance, silver is readily dissolved in 6 N hydrochloric acid while silica is dissolved in concentrated hydrofluoric acid. Dissolution in the presence of sonication is appreciated to facilitate the process. Nanocrystal loading of 1 to 10 percent by weight, depending on the specific nanocrystal dimensions, is sufficient to achieve the desired uniformity and density of pores. Other porous surfaces and methods of manufacture are illustrated in U.S. Pat. No. 7,704,225 and references cited therein, each of which are incorporated herein by reference in their entirety.

It is appreciated that an inner sleeve is optionally coated or impregnated with a first compound. Coating or impregnating optionally provides lubrication so as to ease insertion of the instrument into the skin. A compound optionally: is antibacterial such as those described in WO 2008/060380, the contents of which are incorporated herein by reference; resist or promote cellular adhesion; are anticoagulants or procoagulants; or other desirable compound.

A compound optionally includes factors operable to selectively promote fibroblast growth and/or decrease attachment of bacteria or other contaminants. A compound optionally promotes growth of cells such as fibroblasts. A coating optionally includes the compound fibroblast growth factor (FBF). Optionally, FBF is used in a coating along with insulin and/or dexamethasone. The presence of dexamethasone and/or insulin will promote multiple layer growth of fibroblasts on the surface of or within the pores of a sleeve.

Coating substances illustratively include cell growth scaffolding matrices as detailed in U.S. Pat. Nos. 5,874,500; 6,056,970; and 6,656,496; and Norman et al. Tissue Eng. 3/2005, 11(3-4) pp. 375-386, each of which is incorporated herein by reference. An exemplary coating is a tissue scaffolding, poly-p xylylene, parylene and chemical modified versions of such coatings to enhance post-insertion stabilization. Chemical modifications illustratively include bonding of fibronectin and other molecules implicated in the healing process. While tissue scaffolding and polymers are readily applied by painting, dip coating and spraying, it is also appreciated that polymeric coatings are also readily applied by gas phase deposition techniques such as chemical vapor deposition (CVD). A coating is optionally porous in order to enhance capillary draw. In some embodiments a coating is biodegradable. A coating optionally has pores typically of an average size of between 10 and 500 microns, optionally, of an average size of between 30 and 50 microns.

An outer sleeve of a PAD functions to segregate or deliver vacuum draw pressure to an inner sleeve. The outer sleeve optionally circumferentially and longitudinally covers an inner sleeve. This configuration optionally shields the inner sleeve from epidermal bacterial or other agents upon insertion. An outer sleeve is optionally tapered at one or both ends. Tapering at a distal end (the end nearest the internal end of the catheter during use) provides improved insertion of the instrument into the skin of a subject. A taper may form a smooth interaction with the catheter at the outer sleeve distal end or a ridge is optionally present at or near the site of device interaction with the catheter. An outer sleeve is optionally made of any material suitable for use with a percutaneous instrument. Illustrative materials operable for an outer sleeve include such materials that have a memory or are self-expanding. Materials operable for use as an outer sleeve illustratively include PEBAX, nylons, polyurethanes, polyethylenes (HDPE, UHWPE, LDPE, or any blend of the aforementioned polyethylenes), PET, NiTi, MYLAR, Nickel Titanium Alloy, other polymers such as other thermoplastic polymers, fabrics, silicones such as silicone rubber, latex, glass, or other materials known in the art. An outer sleeve optionally includes or is formed of a scaffold. An outer sleeve scaffold is optionally made of the same or different material as an inner sleeve scaffold. Scaffolds operable for an inner sleeve are similarly operable for an outer sleeve.

It is appreciated that an outer sleeve of the PAD is optionally coated or impregnated with a second compound. A second compound is optionally the same as a first compound. Coating or impregnation optionally provides lubrication so as to ease insertion of the instrument into the skin. A compound optionally: is an antibacterial coating or impregnated material such as those described in WO 2008/060380, the contents of which are incorporated herein by reference, compounds to resist or promote cellular adhesion; anticoagulants or procoagulants; or other desirable compound.

In some embodiments of the PAD, an outer sleeve is textured. A texture is optionally formed of a tissue scaffold. A texture on an outer or inner sleeve optionally has pore sizes, ridges, depressions, indentations, or other texture that is uniform or non-uniform. A texture is optionally of a depth less than 500 nanometers to provide an anchor point for a fibroblast pseudopod extension, while having dimensions that disfavor bacterial colonization. A nanotextured surface as used herein has a uniform distribution of 50 to 500 nanometer median dimension indentations. In some embodiments, the indentations have a median dimension of between 100 and 300 nanometers.

In some embodiments of the PAD an outer sleeve surrounds an inner sleeve. The outer sleeve and inner sleeve are optionally formed from a unitary piece of material. The outer sleeve is optionally oriented surrounding an inner sleeve and optionally is slidably positionable about an inner sleeve. In some embodiments an outer sleeve protects an inner sleeve upon insertion of the inventive instrument and is positionally adjusted relative to the inner sleeve illustratively to a mark or other region that is optionally positioned above the epidermis. In some embodiments the inner sleeve remains traversing the skin while the outer sleeve is positioned above the epidermis or penetrates to one or more desired depths or levels.

An outer sleeve of PAD is optionally positioned external to the skin or near the surface of the skin when the device is employed. It is appreciated that an outer sleeve optionally forms an upper chamber that provides uniform distribution of vacuum pressure into and throughout the inner sleeve or the upper surface thereof. An outer sleeve optionally terminates in or is integral with a collar. A collar is optionally in fluidic connection with a conduit. In some embodiments a collar is made of a material with increased rigidity relative to an outer sleeve.

Without intending to be bound to a particular theory, a surface of a PAD in contact with compromised skin for device insertion promotes intercalation of fibroblasts regardless of whether the surface is textured, coated, or a combination thereof so as to simultaneously promote morphological changes in the fibroblast from circulatory form to dendritic and/or stellate forms through a depth of more than one layer of fibroblast at a time and preferably more than five layers of fibroblasts simultaneously anchoring to the device and more preferably more than ten such layers of fibroblasts. Fibroblast morphological changes simultaneously in more than one layer of such cells serve to rapidly stabilize the percutaneous inventive device. In conjunction with the vacuum pressure draw during the process, infection risks are minimized and a PAD is stabilized against pullout or other device motions relative to the surrounding dermal layers.

A PAD optionally includes one or more gaskets or seals. A seal prevents vacuum pressure from escaping to the atmosphere or from drawing bodily fluid into the system from the subcutaneal end of the instrument. A gasket is optionally made from any material suitable for creating a seal around the circumference of a catheter. A gasket is illustratively made from silicon rubber, latex, nylon, or other polymeric materials. A gasket is optionally connected to or integral with an outer sleeve, an inner sleeve, a bandage, or a collar.

A conduit is optionally fluidly connected to an inner sleeve either via a gasket or direct connection. A conduit is optionally made of any material that will resist total collapse under vacuum pressures used with the invention. A conduit is optionally transected by a valve. A valve is operable to engage, disengage, or adjust the vacuum pressure translated to the inner sleeve. A valve is optionally mechanically or electrically controlled. Any valve or valve system known in the art is operable herein. A valve is optionally positioned at the junction between the conduit and the instrument portions of the PAD.

As mentioned, a PAD may be connected to a vacuum source. A vacuum source can be any source operable for creating negative pressure in or around the device. A vacuum source is optionally a passive vacuum such as a vacuum tube or bottle, or an active vacuum source illustratively a mechanical pump, a syringe, or other vacuum source. A vacuum source optionally applies a continuous or intermittent negative pressure. The magnitude of the negative pressure is optionally adjustable, constant, or variable. In some embodiments an intermittent vacuum is used. Alternatively, a hydrodynamic draw agent is provided that draws fluid from the tissue surrounding through the sleeve via the conduit. A hydrodynamic draw source illustratively includes a super absorbent polymer such as sodium polyacrylate, polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile; high osmotic pressure compositions, such as water soluble salts; and capillary flow draw agents such as dry silica, or other dry hydrophilic powders such cellulosic material. It is noted that recently a diaper filler in the form of a polyacrylic acid as a superabsorbent polymer and a bactericidal skin wash chlorhexidine has been used to draw fluid from the tissue surrounding the sleeve via the conduit. However this approach to fluid draw has limited and exponentially decaying moisture draw.

FIG. 1 illustrates wearable and implanted components of an exemplary prior art cardiac assist system. A PAD 10 serves as an attachment point for an external supply line 12 that supplies air or fluid from a wearable external drive unit (EDU) 14. The EDU 14 is powered by a wearable battery pack 16. Inside the body of the patient, a drive line 18 is attached to the PAD 10 and provides an air or fluid conduit to a cardiac assist device 20.

FIG. 2 depicts a PAD generally at 100 as shown in U.S. Pat. No. 10,258,784 to Kantrowitz. A cap 102 is formed of a material such as silicone, a polymer or a metal and serves to keep debris from entering the device 100. Preferably, the cap 102 is remote from the surface of the epidermis E. The medical appliance 34 depicted as a catheter and vacuum or hydrodynamic draw tubing 104 pass through complementary openings 106 and 108, respectively formed in the cap 102. The tubing 104 provides fluid communication between a vacuum or hydrodynamic draw source 22 and an inner sleeve 12*d*. The inner sleeve 12*d* is characterized by a large and rigid pore matrix 18 in fluid communication to a vacuum source 22 such that the source 22 draws (arrow 22D) tissue fluid and fibroblasts 21 into the sleeve 12*d*. Sleeve 12*d* has a surface 24 that is optionally nanotextured to promote fibroblast adhesion. The surface 24 is optionally decorated with a pattern of contoured cell-conveying channels. It is appreciated that inner sleeve 12*d* optionally includes matrix 26 thereover, a coating substance 27, or a combination thereof. The coating 27 is appreciated to need not cover the entire surface 24. The tissue contacting surface 29 of substance 27 is optionally nanotextured. A flange 112 is provided to stabilize the implanted device 100 within the subcuteanous layer S. The flange 112 is constructed from materials and formed by methods conventional to the art. For example, those detailed in U.S. Pat. Nos. 4,634,422; 4,668,222; 5,059,186; 5,120,313; 5,250,025; 5,814,058; 5,997,524; and 6,503,228.

FIGS. 3A-3C illustrate a modular external interface housing 200 coupled to the PAD 100 as disclosed in U.S. Pat. No. 11,123,472 B2. The modular external interface 200 forms a collar about the neck 110 of the PAD 100 with the main body 216 with a locking feature 218, such as a male extension that engages a female receptacle or cavity as a mechanical overlap connection. In a specific embodiment the main body 216 is made of silicone. The collar seal between the main body 216 and the neck 110 of the PAD 100 forms a hermetic seal with a gasket 230, which in a specific embodiment, is a flexible gasket integrated into the main body 216. In a specific embodiment, the gasket 230 may be a floating gasket. The stabilization of the PAD 100 within the skin to form a germ-free barrier requires subject cells to grow onto the neck surfaces 17 as shown in FIG. 2 of the PAD 100 adjacent to the subject's epidermis E. The neck surface region 17 is adapted to promote growth of autologous fibroblast cells thereon. A suitable exterior side surface substrate for fibroblast growth is a nanotextured polycarbonate (LEXAN®). The modular external interface 200 has a central opening adapted for at least one drive line 220 for insertion into a PAD, and a portal 224 for a vacuum line 222.

The modular external interface 200 is secured and sealed to an outer layer of a patient's skin with a medical dressing. In a specific embodiment the medical dressing is a preform patterned and shaped to conform to the exterior of the modular external interface 200. In a specific embodiment the medical dressing preform may be in two halves (212, 214) that overlap. In a specific embodiment the medical dressing preform may be transparent. In a specific embodiment the medical dressing preform may be made of Tegaderm™ manufactured by Minnesota Mining and Manufacturing Company.

U.S. Pat. No. 10,791,984 entitled "Active Hermeticity Monitoring" to Kantrowitz et al. provides a system and method for measuring and monitoring wound hermeticity and correlating a hermeticity measurement with the establishment of intact biological barrier function of the stratum corneum layer of skin. Embodiments of the method and system for actively assessing hermeticity in wound closure are incorporated into the design of percutaneous skin access devices (PAD), bone anchors, or a wound dressing or bandage alone without at PAD. In a specific embodiment, the hermeticity of the skin wound in the vicinity of the skin-PAD interface is measured as a function of the fluid exudate or transudate egressing from the skin wound in the vicinity of the skin-PAD interface.

As disclosed in U.S. Pat. No. 10,791,984 the degree of hermeticity is related to impedance measurements performed on the skin of a patient. In a specific embodiment, an active impedance measurement may be performed as described in "Impedance measurements of individual surface electrodes" (Medical and Biological Engineering and Computing, November 1983, S. Grimnes) with two electrodes around the collar of a PAD, and/or the active impedance measurements incorporated into the PAD device. Impedance measurement of resistance (R), reactance (Xc), and phase angle (PA) have been shown to be effective in monitoring wound healing closure and infection as disclosed in "Bioelectrical Impedance Assessment of Wound Healing" (Journal of Diabetes Science and Tecchnology, January 2012, Lukaski et al.). As a wound heals resistance (R), reactance (Xc), and phase angle (PA) values increase, and if the wound is infected the values drop. Additional electrode patterns are possible which could further enhance the usefulness of the information.

Furthermore, an assessment of hermeticity may be determined with measurements of humidity in the vacuum line to a PAD. The humidity readings may be taken with impedance humidity sensors. In still other embodiments, local tissue oxygenation in the immediate vicinity of the PAD or other measurements may be used to determine wound healing.

The hermeticity sensor measurement information is readily employed for local closed-loop control of the vacuum supply to the PAD, and to alert the patient with regards to progress or problems with the PAD-skin interface. Additionally, the hermeticity information may be transmitted wirelessly to medical personnel to allow for remote monitoring of the healing wound. For example, as impedance or humidity in a vacuum line stabilizes, medical personnel may be notified that the wound has healed. Alternatively, if the impedance or humidity deviated from expected values, medical personnel could be notified that there may be an infection or a mechanical disruption to the wound; alarms could also be set to notify the patient. In an embodiment, the vacuum supplied to the PAD could automatically be increased or decreased based on the wound healing.

Despite the advances in PAD design and the securement of a PAD to a subject's skin there continues to be a problem of disrupting the formation and maintaining of skin layers about the PAD with respect to flexible or pliable drivelines during the healing process. In addition, while vacuum pumps, capillary draw, and hydrodynamic draw have been used reduce the pressure on the insertion site and thereby dry the insertion site to stimulate granulation that will mechanically stabilize the appliance and reduce the prospect of infection; infection at the site of PAD used with pliable and flexible drivelines continues to occur as the seal between the layers of skin and the bendable driveline tends to either not fully form or fails as the driveline flexes at the insertion site.

Furthermore, there continues to ne be a need to adjust pressure to preclude skin prolapse (pucker) around a PAD.

There is a continuing need for improved percutaneous access devices that are equipped with improved environmental controls, pressure controls, and feedback that encourage and expedite nascent layers of skin that are being formed during the healing process, as well as maintaining an infection preventive seal around percutaneous access devices.

SUMMARY OF THE INVENTION

A system is provided for measuring and monitoring environmental conditions of a wound of a patient. The system includes one or more sensors for measuring parameters that correlate to a degree of wound healing, and at least one of an air filter in fluid communication with the wound. The one or more sensors are incorporated into the design of a percutaneous skin access device (PAD), a bone anchor, a wound dressing, or a bandage.

A method is provided for measuring and monitoring wound conditions of a patient. The method includes placing one or more sensors for measuring parameters that correlate to a degree of wound healing on the skin of a patient; where the one or more sensors are incorporated into the design of a percutaneous skin access device (PAD), a bone anchor, a wound dressing, or a bandage.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which like reference numerals refer to like parts throughout the several views, and wherein:

DETAILED DESCRIPTION OF THE INVENTION

Figure 1:
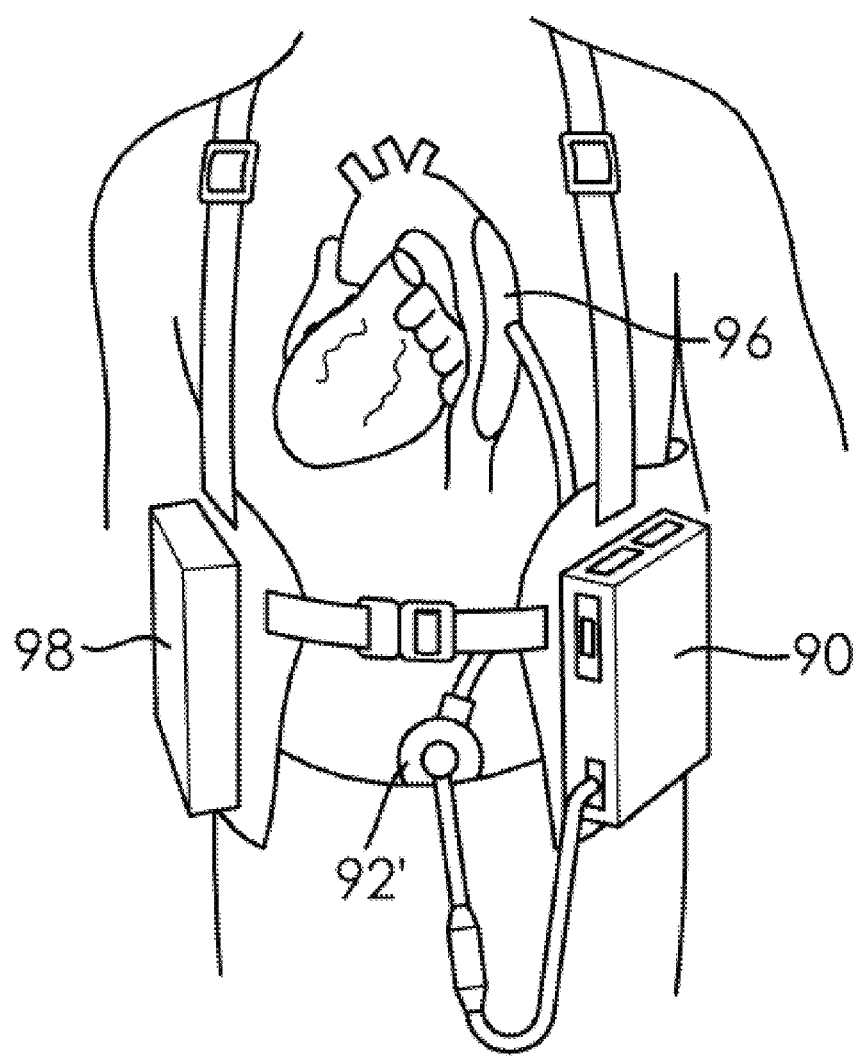
FIG. 1 illustrates prior art wearable and implanted components of a cardiac assist system with a percutaneous access device (PAD) and internal driveline.
Figure 2:
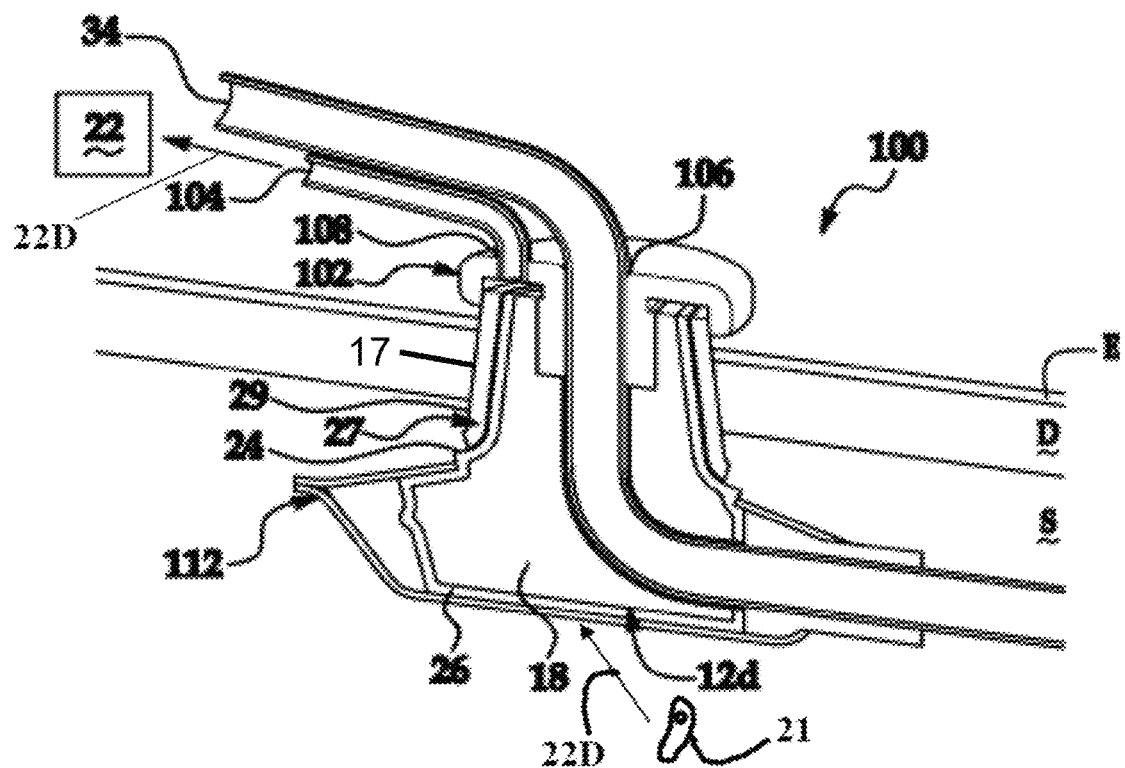
FIG. 2 is a prior art, partial cutaway view of a flanged percutaneous access device (PAD) with relative dimensions of aspect exaggerated for visual clarity.

Embodiments of the invention provide percutaneous access devices (PAD), bandages, or other implantable medical devices that are equipped with filters, environmental controls, and sensors that promote the formation of a natural biologic seal between the skin and the device to form a barrier to microbial invasion into the body. Percutaneous access devices may also illustratively be used for other devices including peritoneal dialysis catheters, Steinman pin, Kirschner wires, and chronic indwelling venous access catheters that require skin penetration.

It is noted that previous efforts have concentrated on removing moisture or humidity from wound areas, however a level of moisture is required to allow fibroblasts to actively attach to an implanted PAD and to promote the establishment of intact biological barrier function of the stratum corneum layer of skin. It is also noted that moisture and pressure levels may be needed to change as the wound healing process progresses through different stages. It is further noted that pressure levels may require adjustment to preclude skin prolapse around an implanted device.

Embodiments of the invention monitor and dynamically control levels of humidity and pressure to optimize wound closure about an implanted device or when a PAD is not present a wound itself. Embodiments of the method and system for actively assessing wound closure are incorporated into the design of percutaneous skin access devices (PAD), bone anchors, or a wound dressing or bandage alone without at PAD. The pressure and humidity sensor provide active feedback for making changes to the ecology of the wound site or PAD insertion site. In specific inventive embodiments a filter, which illustratively includes a submicron filter, is used to aerate the wound while also preventing pathogens in the ambient air from reaching the wound.

In certain embodiments of the present invention, an assessment of hermeticity may be determined with measurements of humidity in the vacuum line to a PAD. The humidity readings may be taken with impedance humidity sensors. In still other embodiments, local tissue oxygenation in the immediate vicinity of the PAD or other measurements may be used to determine wound healing.

The hermeticity measurement parameters are readily communicated by wired or wireless connection to a computing or communication device for immediate or remote monitoring. Known and future wireless standards and protocols such as, but not limited to, Bluetooth, Zigbee, WiFi, and others may be used to transmit hermeticity measurements. Remote monitoring may be facilitated via an Internet or cellular network enabled device in communication with the output of a hermeticity measurement device or sensor. The hermeticity measurement devices or sensors may require an external power source such as a battery, or may be passive elements such as radio frequency identification elements (RFID), which obviate the need for an electrical power source to be directly incorporated into the PAD. A passive RFID element retransmits a signal using the energy of an incoming interrogation signal, where in embodiments of the inventive hermeticity sensor the transmitted signal will vary in frequency or phase with the impedance or humidity measurement. In certain embodiments, battery power used to supply the vacuum source of the PAD may also be utilized to supply power to the one or more hermeticity sensors.

The hermeticity sensor measurement information is readily employed for local closed-loop control of the vacuum supply to the PAD, and to alert the patient with regards to progress or problems with the PAD-skin interface. Additionally, the hermeticity information may be transmitted wirelessly to medical personnel to allow for remote monitoring of the healing wound. For example, as impedance or humidity in a vacuum line stabilizes, medical personnel may be notified that the wound has healed. Alternatively, if the impedance or humidity deviated from expected values, medical personnel could be notified that there may be an infection or a mechanical disruption to the wound; alarms could also be set to notify the patient. In an embodiment, the vacuum supplied to the PAD could automatically be increased or decreased based on the wound healing.

In specific inventive embodiments integrated multi-lumen tubing as disclosed in PCT Application PCT/US2020/060668 to Kantrowitz is used for delivering a vacuum. Integrated multi-lumen tubing provides a combination of intravenous (IV) infusion lines, vacuum lines, and in some instances monitoring lines for attachment to a percutaneous access device or long term implant. The integration of the intravenous infusion lines, vacuum lines, and monitoring lines that connect to the PAD and other inserted instruments organizes the myriad of intravenous infusion lines, vacuum lines, and monitoring lines that connect to the PAD and other inserted instruments that tend to get tangled, interfere with patient comfort and movement, and are potentially difficult for health care workers to change and maintain. Furthermore, by using the lines associated with the IV already present in a hospital or medical facility allows for use of the existing vacuum source used in the facility.

Figure 4:
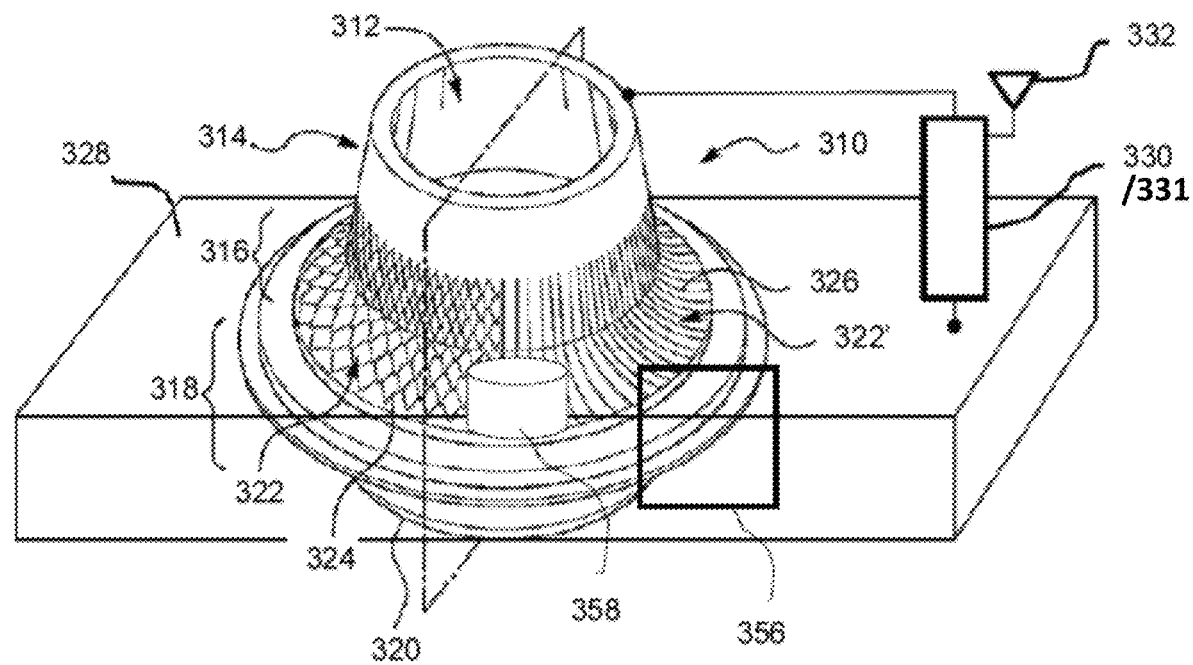
FIG. 4 is a composite perspective view depicting two exemplary cell growth channel pattern halves of an inventive percutaneous access device with an environmental sensor, an air filter, and a viewing window, where the cell growth channels are not depicted to scale for visual clarity in accordance with embodiments of the invention.

Referring now to the figures, FIG. 4 illustrates a prior art PAD 310 coupled to a hermeticity and/or pressure sensor 330. A separate sensor 331 is included in some embodiments to detect hyperemia associated with an infection associated with the PAD 310. It is appreciated that the sensor 330 may combine pressure and humidity measurements, or separate sensors units may take pressure and humidity measurements. The stabilization of the PAD 310 within the skin to form a germ-free barrier requires subject cells to grow onto the neck surfaces 316 of the PAD 310 adjacent to the subject's epidermis 328. The PAD portal 310 has an opening 312 defined by a sidewall 314, the exterior side of the wall 314 defining a neck region 316 adapted to promote growth of autologous fibroblast cells thereon. A suitable exterior side surface substrate for fibroblast growth is a nanotextured polycarbonate (LEXAN®). Beneath the neck region 316 lies an implanted region 318 terminating in an inward portal face 320, that is communicative with the opening 312 to form a passage through which fluids, electrical signals, gases, or a combination thereof are communicated. The neck region 316 has a pattern of contoured autologous cell-conveying channels 322 or 322'. It is appreciated that the channels may take a variety of forms. In the figures, a linear channel 324 and a chrysanthemum-pattern channel 326 are depicted in composite halves as defined by the dashed plane. It is appreciated that an operative device typically would have a pattern 324 or 326 circumferentially decorating the device surface. Other channel patterns operative herein include any pattern that disfavors bacterial pocket formation. Optionally, a vacuum is drawn toward an upward region of the neck region 316 in order to actively draw blood plasma and fibroblasts contained therein along the channels 322 to further facilitate autologous cell growth on the neck region 316. Sensor 330 is operative to measure changes in impedance between the PAD 310 and the patient's skin 328 so as to determine hermeticity for the implanted PAD 310. Sensors 330/331 has wireless communication capabilities as represented by antenna 332 for transmitting sensor readings. As shown an observation window 356 allows a healthcare provider to assess the condition of the wound without disturbing the vacuum seal. A filter 358 in fluid communication with the wound site provides filtered air that is free of pathogens and aerates the wound.

Figure 5:
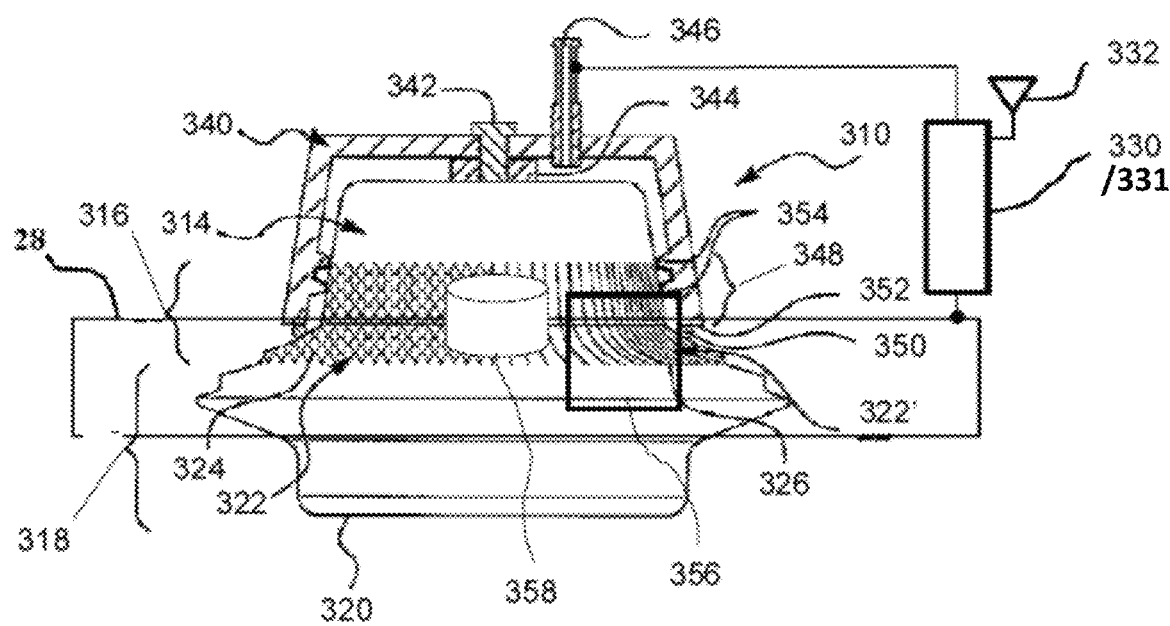
FIG. 5 is a plan view of the percutaneous access device depicted in FIG. 4 with a cross-sectional view along with a cross-sectional view of a vacuum manifold coupled thereto, and a sensor for detecting humidity levels in the vacuum line in accordance with embodiments of the invention.

FIG. 5, show a prior art view of a vacuum manifold 340 that is secured to a portal 310 by way of a fastener 342. The fastener 342 extends into a temporary seating pin (not shown) to fit within the opening 312. A spacer 344 assures a uniform gap between the manifold 340 and the neck region 316. An inlet 346 is provided for the coupling of the manifold 340 to a vacuum source. Manifold 340 has an extending lip 48 that terminates proximal to a surface of the neck portion 316 at at least one point amenable to form a seal 350 with the surrounding subject skin or a gel applied to the user skin. It is appreciated that a retaining groove 354 is defined on a lip surface in opposition to the portal neck portion 316, the retaining groove 354 amenable to seat a vacuum gasket between the manifold 340 and the neck portion 316. A gasket used herein is formed of conventional materials illustratively including neoprene. While the skin seal 350 is suitable to draw a vacuum around the periphery of the neck portion 316, cells that are drawn within the portal portion under vacuum tend to be drawn to a surface of the neck portion 316 as opposed to intercalating within a channel or a matrix coating. As such, it is appreciated that while drawing a vacuum at the interface between the neck portion 316 and lip terminus 352 is suitable to urge an initial population of cells into the channels 322, drawing of cells to the uppermost reaches of channels 322 preferably occurs by forming a vacuum seal between the manifold 340 and the neck portion 316 that includes only the uppermost terminus of the channels 322. It is appreciated that once cells begin to adhere to a surface defining a portion of a channel 322, abrasion and indeed contact with that surface is preferably avoided. It is further appreciated that a retaining groove 354 and the ensuing vacuum seal formed between the manifold 340 and the neck portion 316 is readily moved relative to the neck portion 316 by varying the thickness of the spacer 344. While the manifold 340 is beneficial in drawing serum and the fibroblasts contained therein through the channels 322 in the neck portion 316, it is also appreciated that independent of vacuum, the manifold 340 also serves to provide a mechanical guard to protect growing cells on the neck portion 316. To this end, it is appreciated that an inlet 346 can be connected to a gas supply such as air or oxygen to promote autologous cell growth and granulation about the neck portion 316; or liquid solutions fostering cell growth are also provided and illustratively include autologous plasma, fibroblast growth enhancing solutions, and antimicrobials. Sensor 330 can determine hermeticity with measurements of humidity in the vacuum line 346 to the PAD 310. Alternatively, the sensor 330 may determine the hermeticity of the skin wound in the vicinity of the skin-PAD interface as measured as a function of the fluid exudate or transudate egressing from the skin wound in the vicinity of the skin-PAD interface. Sensor 330 may also measure pressure at the wound site. As shown an observation window 356 allows a healthcare provider to assess the condition of the wound without disturbing the vacuum seal. A filter 358 in fluid communication with the wound site provides filtered air that is free of pathogens and aerates the wound.

Figure 6:
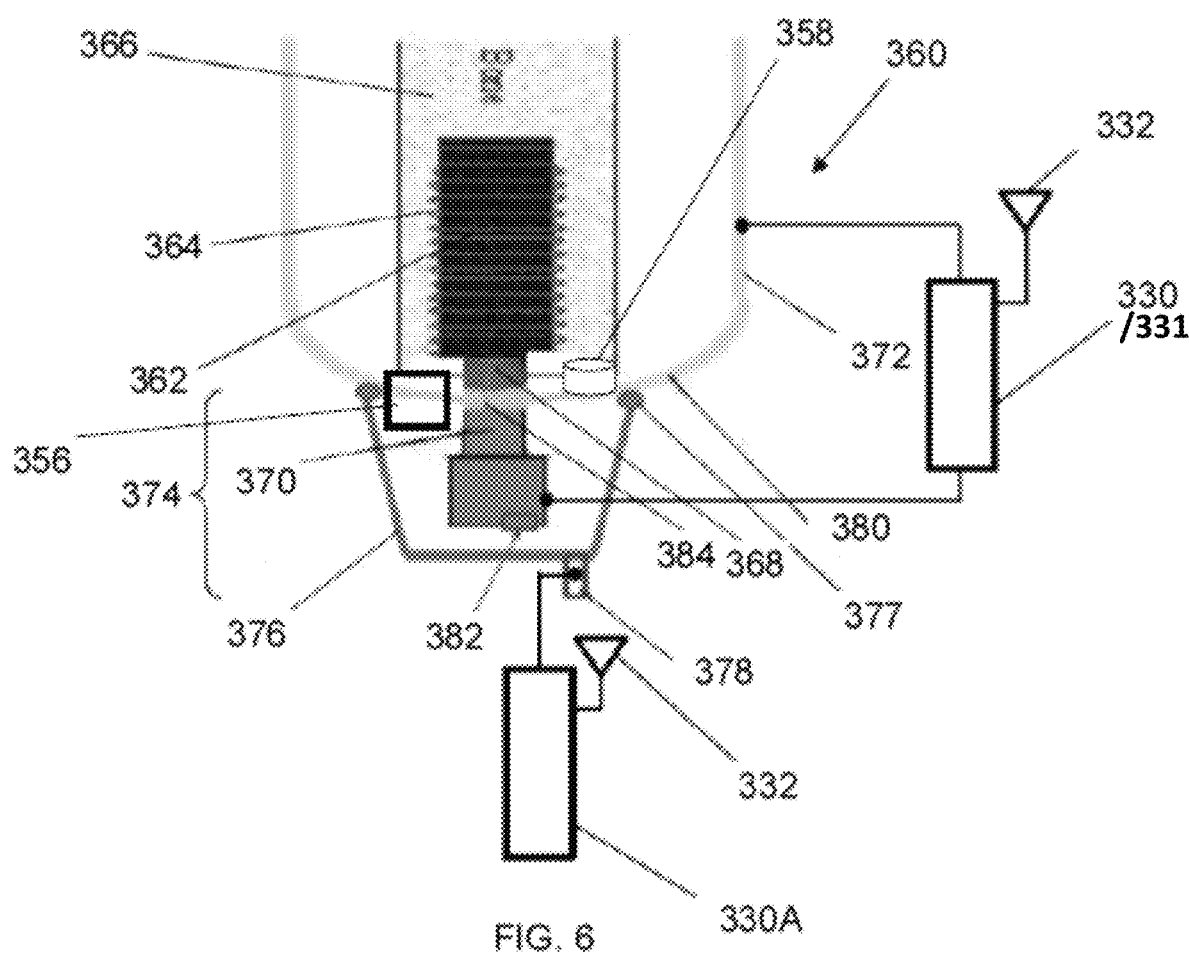
FIG. 6 illustrates a side sectional view of a bone anchor implanted in a bone with an attached abutment and negative pressure manifold applied and outfitted with a viewing window, air filter, pressure sensor and/or a hermeticity sensor for detecting resistance between the skin and a bone implant, and a sensor for detecting humidity in the vacuum line in accordance with embodiments of the invention, a hyperemia sensor is also optional provided to detect possible infection.

FIG. 6 illustrates a bone anchor system 360 coupled to a sensor 330. The bone anchor system 360 includes the bone anchor 362 with a threaded screw portion 364 that engages and anchors into the bone 366 with a neck portion 368 extending out of the bone 366 and configured to mechanically engage an abutment 370 and biologically meld or engage with an epidermal or gum layer 372. The bone anchor system 360 also includes a negative pressure system 374 including a manifold 376 with an access point or inlet 378 that is fitted over the terminus or stump 380 of the wounded limb or region that encompasses the insertion point of the bone anchor 362. Manifold 376 may also be representative of a wearable dental appliance. Gasket 377 along the perimeter edge of the manifold 376 acts as a seal to the epidermal or gum layer 372. Access point 378 is configured to connect to a vacuum device for vacuum therapy in order to remove exudate and directly appose both soft and hard tissue to the bone anchor 362 and neck portion 368. Vacuum access 382 provides negative pressure access to microtexture/bone site interface of the neck portion 368 and is sealed following use. Tissue scaffold matrix 384 is a coating applied to the neck region 368 prior to implantation also that facilitates and promotes cell growth of autologous fibroblast cells thereon to make a seal with the epidermal or gum layer 372. A suitable exterior side surface substrate for fibroblast growth is a nanotextured polycarbonate (LEXAN®). Sensor 330 is operative to measure changes in impedance between the bone anchor 362 and the patient's epidermal or gum layer 372 so as to determine hermeticity for the implanted bone anchor 362. Sensor 330 may also measure pressure at the wound site. Sensor 330 has wireless communication capabilities as represented by antenna 332 for transmitting sensor readings. Sensor 330A may determine hermeticity with measurements of humidity in the vacuum line or access point 378 to the bone anchor system 360. As shown an observation window 356 allows a healthcare provider to assess the condition of the wound without disturbing the vacuum seal. A filter 358 in fluid communication with the wound site provides filtered air that is free of pathogens and aerates the wound.

Figure 3A:
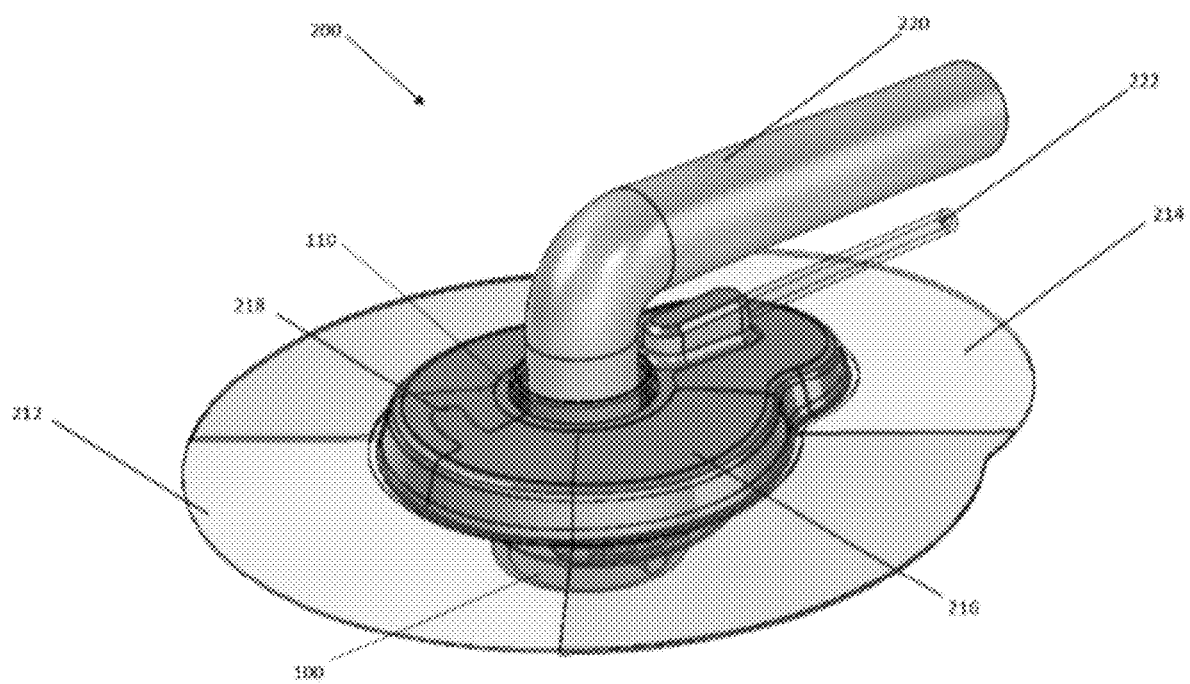
FIGS. 3A-3C are perspective views of a prior art modular external interface seal for a PAD appliance secured with adhesive dressings to a subject.
Figures 3B, 3C:
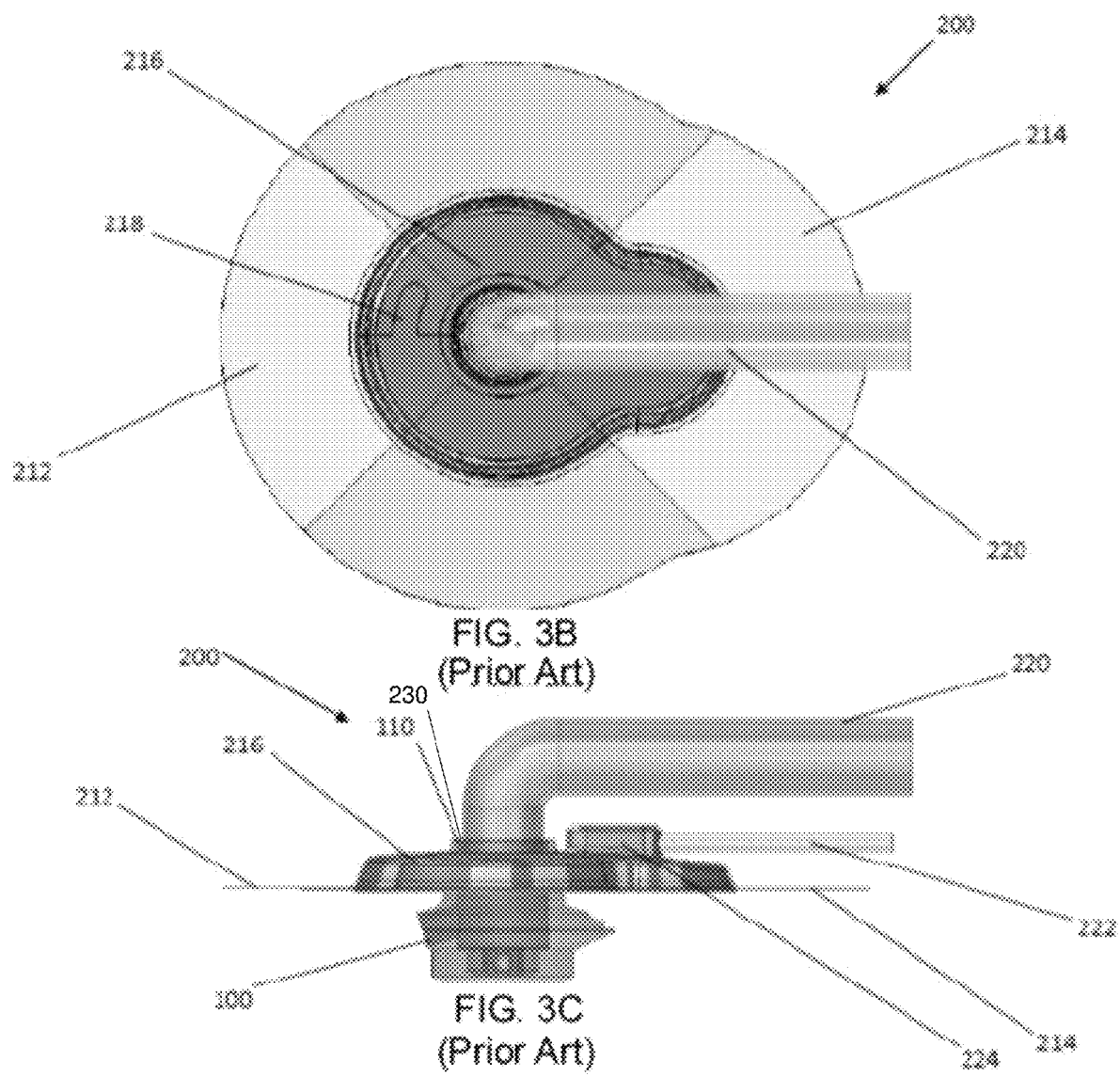
Figure 7:
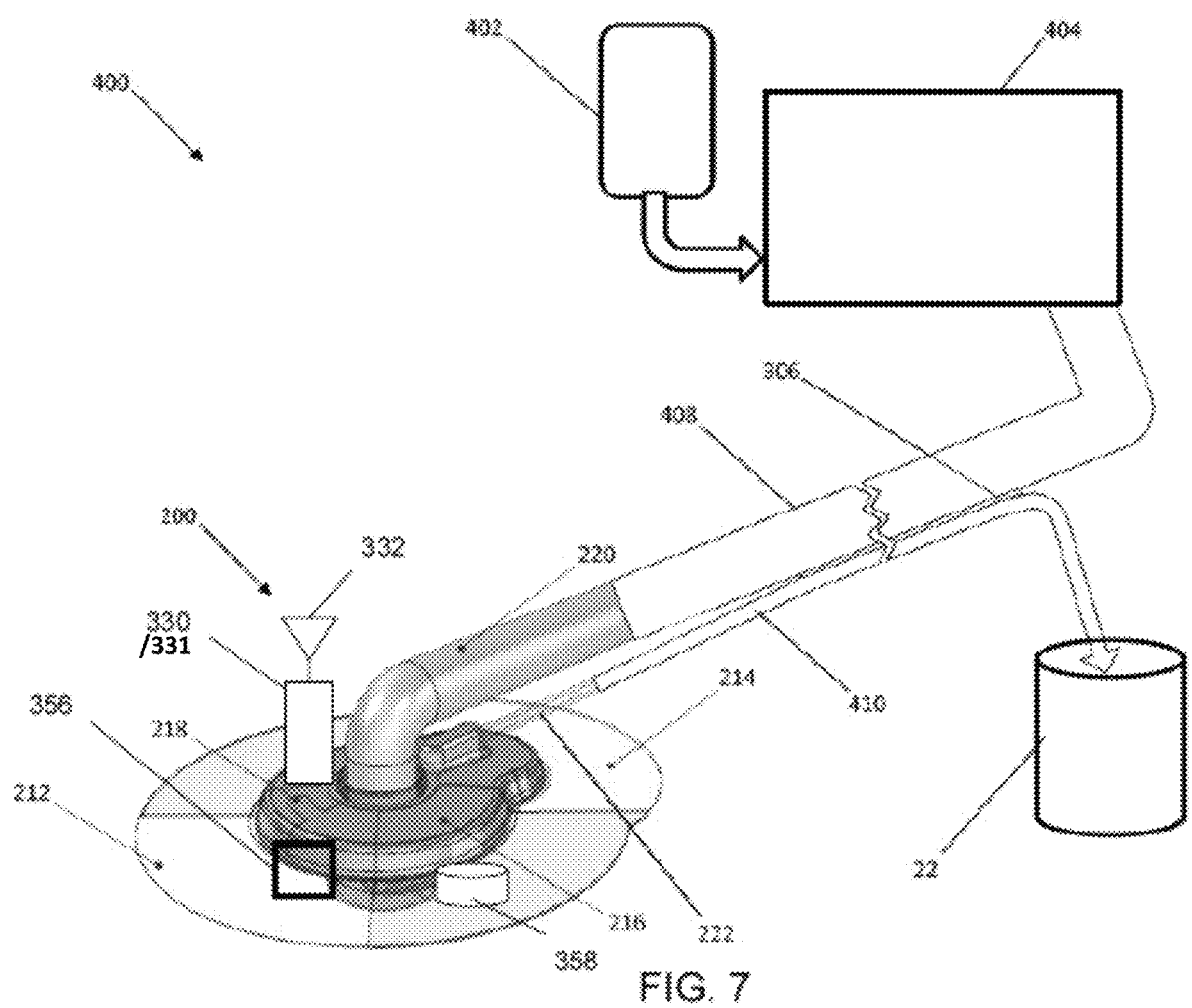
FIG. 7 illustrates a system for suppling intravenous fluids and a vacuum via an integrated muti-lumen tubes to the modular external interface seal of FIGS. 3A-3C for PAD appliances equipped with environmental sensors, an air filter, and a viewing window in accordance with embodiments of the invention.

FIG. 7 illustrates a system 400 for suppling intravenous (IV) fluids and a vacuum via an embodiment of the integrated muti-lumen tubes to the modular external interface seal 200 of FIGS. 3A-3C for PAD appliances. An intravenous bag or bottle 402 is shown supplying an infusion pump 404. The IV fluids are supplied via an infusion line 408 to the driveline 220 of the PAD 200. A vacuum line 410 attached to the infusion line 408 with web 306 terminates in a vacuum pump 22 and the vacuum line 222 of the PAD 200. The system 400 further includes sensor 330 that may determine hermeticity with measurements of humidity in the vacuum line 222 to the PAD 200. Alternatively, the sensor 330 may determine the hermeticity of the skin wound in the vicinity of the skin-PAD interface as measured as a function of the fluid exudate or transudate egressing from the skin wound in the vicinity of the skin-PAD interface. Sensor 330 may also measure pressure at the wound site. In still other embodiments, a sensor 331 detects hyperemia as an indicator of infection at or proximal to the interface. The sensor 331 inclusive a thermometer, infrared camera, or a combination thereof. In still other inventive embodiments, thermal photography through the observation window with a devoted or smartphone associated thermal camera is part of operation monitoring protocol. As shown an observation window 356 allows a healthcare provider to assess the condition of the wound without disturbing the vacuum seal. A filter 358 in fluid communication with the wound site provides filtered air that is free of pathogens and aerates the wound.

Figure 8:
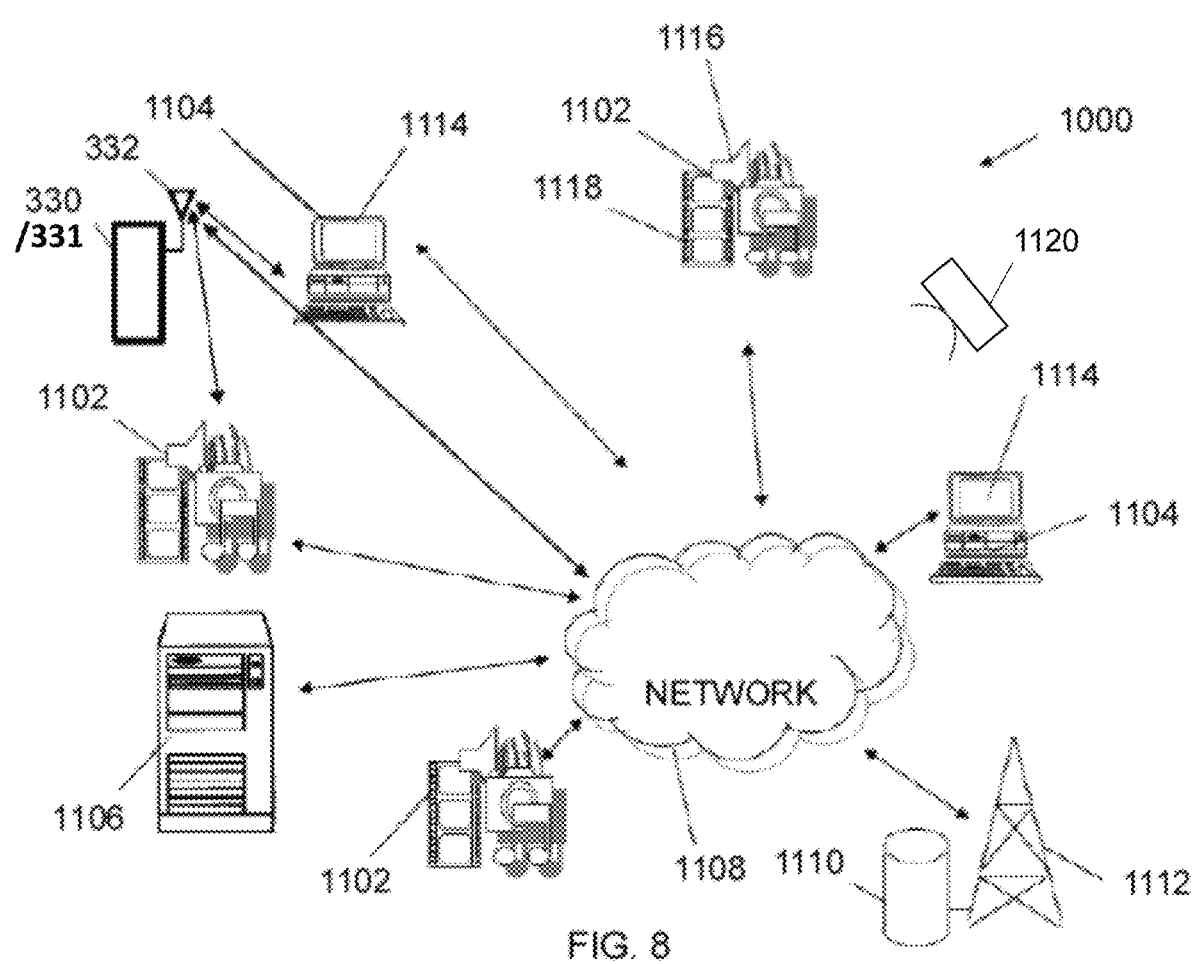
FIG. 8 is a schematic diagram illustrating an overall view of communication devices, computing devices, and mediums for implementing embodiments of the invention.

FIG. 8 is a schematic diagram illustrating an overall view of communication devices, computing devices, and mediums for implementing the hermeticity and or hyperemia measuring and monitoring platform according to embodiments of the invention. The elements of the embodiments of FIGS. 4-7 are included in the networks and devices of FIG. 8.

The system 1000 includes multimedia devices 1102 and desktop computer devices 1104 configured with display capabilities 1114 and processors for executing instructions and commands. The multimedia devices 1102 are optionally mobile communication and entertainment devices, such as cellular phones and mobile computing devices that in certain embodiments are wirelessly connected to a network 1108. The multimedia devices 1102 typically have video displays 1118 and audio outputs 1116. The multimedia devices 1102 and desktop computer devices 1104 are optionally configured with internal storage, software, and a graphical user interface (GUI) for carrying out elements of the hermeticity and or hyperemia measuring and monitoring platform according to embodiments of the invention. The network 1108 is optionally any type of known network including a fixed wire line network, cable and fiber optics, over the air broadcasts, satellite 1120, local area network (LAN), wide area network (WAN), global network (e.g., Internet), intranet, etc. with data/Internet and remote storage capabilities as represented by server 1106. Communication aspects of the network are represented by cellular base station 1110 and antenna 1112. In a preferred embodiment, the network 1108 is a LAN and each remote device 1102 and desktop device 1104 executes a user interface application (e.g., Web browser) to contact the server system 1106 through the network 1108. Alternatively, the remote devices 1102 and 1104 may be implemented using a device programmed primarily for accessing network 108 such as a remote client. Hermeticity/hyperemia/pressure sensor 330 may communicate directly with remote devices 1102 and 1104 via near field communication standards such as Bluetooth or Zigbee, or alternatively via network 1108.

The software for the platform, of certain inventive embodiments, is resident on multimedia devices 1102, desktop or laptop computers 1104, or stored within the server 1106 or cellular base station 1110 for download to an end user. Server 1106 may implement a cloud-based service for implementing embodiments of the platform with a multi-tenant database for storage of separate client data.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention but is not meant to be a limitation upon the practice thereof. The following claims, including all equivalents thereof, are intended to define the scope of the invention.

The invention claimed is:

1. A system for monitoring an environmental condition of a wound on a patient's skin comprising:
   an inlet for a vacuum source in communication with the wound;
   a vacuum seal surrounding the wound on the patient's skin;
   an observation window to assess the condition of the wound without disturbing the vacuum seal;
   one or more sensors for measuring parameters that correlate to a degree of wound healing or infection;
   at least one of an air filter in fluid communication with the wound; and
   wherein said one or more sensors are incorporated into the design of a percutaneous skin access device (PAD), a bone anchor, a wound dressing, or a bandage.

2. The system of claim 1 wherein the environmental condition of the wound is related to impedance measurements performed on the patient's skin.

3. The system of claim 1 wherein said one or more sensors further comprise two electrodes positioned at the interface of said PAD or said bone anchor and the patient's skin.

4. The system of claim 1 wherein said one or more sensors determine a degree of wound hermeticity via measurements of local tissue oxygenation in the immediate vicinity of said PAD or said bone anchor interface with the patient's skin alone or in combination with thermal sensing of the patient's skin for hyeremia.

5. The system of claim 1 wherein said environmental conditions are communicated by wired or wireless connection to a computing or a communication device for immediate or remote monitoring.

6. The system of claim 1 wherein said one or more sensors require an external power source.

7. The system of claim 6 wherein said external power source is a battery used to supply a vacuum source to said PAD or said bone anchor.

8. The system of claim 1 wherein said one or more sensors are passive elements which do not require an external power source.

9. The system of claim 8 wherein said passive elements are radio frequency identification elements (RFID).

10. The system of claim 1 wherein said sensor parameters are employed for local closed-loop control of a vacuum supply to said PAD or said bone anchor.

11. The system of claim 1 further comprising an observation window providing a view of the wound.

12. A method for monitoring wound conditions of a patient's skin comprising:
    placing one or more sensors for measuring parameters that correlate to a degree of wound healing or infection on the patient's skin; and
    exposing a wound on the patient's skin to a filtered air in an enclosed environment being sampled by said one or more sensors; and
    measuring the parameters from said one or more sensors;
    wherein said one or more sensors are incorporated into the design of a percutaneous skin access device (PAD), a bone anchor, a wound dressing, or a bandage.

13. The method of claim 12 wherein said degree of wound healing is related to impedance measurements performed on the patient's skin.

14. The method of claim 12 wherein said placing of said one or more sensors further comprises positioning two electrodes at an interface of said PAD or said bone anchor and the patient's skin.

15. The method of claim 12 wherein said one or more sensors determine said degree of wound healing via measurements of humidity in a vacuum line to said PAD or said bone anchor.

16. The method of claim 12 wherein said one or more sensors determine a degree of wound hermeticity via measurements of local tissue oxygenation in the immediate vicinity of said PAD or said bone anchor interface with the patient's skin.

17. The method of claim 12 wherein said wound conditions are communicated by wired or wireless connection to a computing or a communication device for immediate or remote monitoring.

18. The method of claim 12 wherein said sensor parameters are employed for local closed-loop control of a vacuum supply to said PAD or said bone anchor.

19. The method of claim 12 further comprising taking a thermal camera image through a transparent observation window of the PAD, the bone anchor, the wound dressing, or the bandage to detect hyperemia.

* * * * *